(12) United States Patent
Sørensen et al.

(10) Patent No.: US 6,805,781 B2
(45) Date of Patent: Oct. 19, 2004

(54) ELECTRODE DEVICE WITH A SOLID STATE REFERENCE SYSTEM

(75) Inventors: Poul Ravn Sørensen, Copenhagen (DK); Birgit Zachau-Christiansen, Copenhagen (DK)

(73) Assignee: Radiometer Medical A/S, Bronshoj (DK)

( * ) Notice: Subject to any disclaimer, the term of this patent is extended or adjusted under 35 U.S.C. 154(b) by 204 days.

(21) Appl. No.: 10/233,819

(22) Filed: Aug. 29, 2002

(65) Prior Publication Data

US 2004/0163949 A1 Aug. 26, 2004

Related U.S. Application Data

(63) Continuation of application No. PCT/DK01/00139, filed on Mar. 1, 2001.

(30) Foreign Application Priority Data

Mar. 1, 2000 (DK) .................................... 2000 00327

(51) Int. Cl.⁷ ............................................. G01N 27/26
(52) U.S. Cl. ........................ 204/416; 204/419; 204/435
(58) Field of Search ................................ 204/419, 433, 204/435, 416

(56) References Cited

U.S. PATENT DOCUMENTS

| | | | |
|---|---|---|---|
| 3,825,482 A | 7/1974 | Wechter et al. | |
| 3,853,731 A | 12/1974 | Gray et al. | |
| 3,856,634 A | 12/1974 | Hahn et al. | |
| 4,632,732 A | 12/1986 | Fog et al. | |

(List continued on next page.)

FOREIGN PATENT DOCUMENTS

| | | |
|---|---|---|
| DE | 2 002 676 | 11/1970 |
| DE | 25 38 739 | 3/1976 |
| DE | 41 2 301 A1 | 10/1992 |
| DE | 43 24 922 A1 | 2/1995 |
| EP | 0 498 572 A2 | 8/1992 |
| EP | 0 927 884 A2 | 7/1999 |
| GB | 1 470 558 | 4/1977 |
| GB | 1 521 964 | 8/1979 |
| GB | 1 597 493 | 9/1981 |
| GB | 1 602 564 | 11/1981 |
| WO | WO 83/03304 | 9/1983 |
| WO | WO 95/22050 | 8/1995 |
| WO | WO 96/12944 | 5/1996 |

OTHER PUBLICATIONS

West, et al., "Solid–State Sodium Cells—An Alternative to Lithium Cells?," *J. Power Sources*, pp. 59–67 (1989).

Skaarup, et al., "Solid State Sodium Batteries," Physics Laboratory III, Institute of Physical Chemistry, Technical University of Denmark, D–2800 Lyngby, Denmark, Abstract, pp. 75–86.

*Primary Examiner*—Bruce F. Bell
(74) *Attorney, Agent, or Firm*—Maurice B. Stiefel; Bryan Cave LLP (57) ABSTRACT

The invention concerns an electrode device comprising an ion selective material, a solid state, inner reference system of sodium vanadium bronze and a contact material, where sodium may be reversibly intercalated, in the bronze. Such an electrode device may for instance be sensitive to ions, such as $H^+$, $Na^+$, $K^+$ and $Ca^{2+}$. It may also include a reactive material in which a particular analyte is reacted to form an ion product, to which the ion selective material is sensitive, such as in electrode devices of the Severinghaus-type or in biosensors. The electrode device according to the invention can be prepared by thick film printing.

26 Claims, 4 Drawing Sheets

U.S. PATENT DOCUMENTS

| | | |
|---|---|---|
| 4,798,664 A | 1/1989 | Yamaguchi et al. |
| 4,816,118 A | 3/1989 | Oyama et al. |
| 4,839,020 A | 6/1989 | Yamaguchi et al. |
| 4,861,454 A | 8/1989 | Ushizawa et al. |
| 4,871,442 A | 10/1989 | Yamaguchi et al. |
| 4,981,570 A | 1/1991 | Yamaguchi et al. |
| 5,041,792 A | 8/1991 | Thompson |
| 5,112,456 A | 5/1992 | Worrell et al. |
| 5,122,254 A | 6/1992 | Ammende et al. |
| 5,139,626 A | 8/1992 | Yamaguchi et al. |
| 5,192,417 A | 3/1993 | Oyama et al. |
| 5,286,365 A | 2/1994 | Shu |
| 5,326,452 A | 7/1994 | Roed et al. |
| 5,552,032 A | 9/1996 | Xie et al. |
| 5,910,239 A | 6/1999 | Maier et al. |
| 5,911,862 A | 6/1999 | Chan |
| 6,015,481 A * | 1/2000 | Greenblatt et al. ......... 204/419 |

* cited by examiner

ELECTRODE DEVICE WITH A SOLID STATE REFERENCE SYSTEM

This application is a continuation division of international application number PCT DK01/00139, filed 1 Mar. 2001.

The present invention concerns an electrode device comprising an ion selective material, a solid state, inner reference system of a bronze and a contact material, where the reference system mediates the electrochemical correspondence between the ion selective material and the contact material. More specifically, the invention concerns a planar, miniaturised electrode device with a solid state, inner reference system.

In many cases it is interesting to analyse samples for content or presence of different ions. For this purpose, electrode devices often include an ion selective membrane, an inner reference system and a contact material, which is connected with usual measuring equipment together with an external reference electrode. The inner reference system mediates the electrochemical correspondence between the ion selective membrane and the contact material, and it has the purpose of maintaining a stable inner electrochemical potential.

As inner reference system, conventional electrode devices comprise a metal dipped in into an electrolyte liquid. The equilibrium reaction between the metal ion of the reference system and the anion of the electrolyte liquid normally takes place via a solid metal salt of these ions, which salt is deposited on the metal. These types of reference systems containing a liquid are stable and reliable in use, but they have some disadvantages. They are relatively fragile, cannot be used at high temperatures, has a storage stability which is limited by evaporation of the electrolyte liquid, and they also limit the possible methods of manufacture due to the fluid electrolyte and the relatively large volume of electrolyte liquid which is required to achieve a sufficient stability for the system. If the volume of the electrolyte liquid is reduced substantially, the system becomes sensitive to redox active substances-and carbon dioxide. The conventional reference systems are actually unsuitable for miniaturisation. Attempts to reduce or avoid these disadvantages have lead to the development of electrode devices with a solid state, inner reference system.

Certain properties of the reference system are thought to have a stabilising effect on its potential. Thus, the ability of the reference system to take up and liberate electrons across a phase boundary Influences the stability of said reference system. The uptake and liberation of electrons typically take place between two phases in the system or between the system and the surroundings and result in a so-called exchange current. It also promotes the stability, if the reaction(s) implicating the uptake/liberation of the electrons are reversible and occur to such extent that the magnitude of the exchange current does not have a limiting effect.

In the literature, several solid state, inner reference systems are described. In one type of reference systems, the same metals and salts are used as in the conventional inner reference systems, but the salts are dissolved in hydrocolloids or other highly-viscous materials with water activity. As the conventional reference systems, these types of reference systems will, if miniaturised, be sensitive to redox active substances and to carbon dioxide present. Their use at high temperatures is also limited. Examples of such inner reference systems are described in e.g. U.S. Pat. Nos. 5,911,862, 5,552,032 and 5,041,792.

In another type of reference system, a redox active substance (e.g. a conventional redox pair or a redox polymer) is immobilised in the membrane or between the membrane and the contact material. The contact material often consists of a precious metal, but can also consist of graphite. The redox active groups may be incorporated in the membrane or constitute a layer between the contact material and the membrane. This type of reference system will typically be sensitive to redox active substances present. Examples of such inner reference systems are described in e.g. EP 498 572; U.S. Pat. Nos. 5,286,365; 5,326,452; 4,871,442; 4,981,570; 4,798,664; 4,816,118; 5,139,626; 5,192,417 and EP 927 884. Among these, typical examples of this type of solid state, inner reference system are EP 498 572, wherein a fortiophore is used for complex binding in the membrane of the ion present in the contact material, U.S. Pat. No. 5,286,365, wherein an electrode device is described in which a reference layer comprising a redox pair is placed between the contact material and the membrane, and U.S. Pat. No. 5,326,452 in which the electrode device has a reference system of iron oxide, and where iron oxide is also incorporated in the glass membrane. This electrode device can be prepared by thick film printing.

In a third type of reference system, a solid state reference system is used which possesses both electron conductivity and ion conductivity. This material may typically be a bronze or another metal oxide. In this case, the stable, inner potential is achieved by an exchange current between bronze/metal oxide and the membrane, and it can be further stabilised if two phases are present in the bronzelmetal oxide.

In GB 1 470 558 such electrode device for determining components in solid or fluid metals or alloys is described. It is especially used for determining sodium in such metals or alloys. The reference system of the electrode device comprises a solid state electrolyte of β-aluminium oxide containing the component which is to be determined, or it comprises the component which is to be determined in solid state, covered by the above-mentioned electrolyte for protection of the solid state reference system. The reference system should preferably have two phases. DE 25 38 739 (GB 1 521 964) and GB 1 602 564 disclose electrode devices, which are further developments of the above-mentioned electrode device. In DE 25 38 739 the reference system includes tungsten bronze or mercury amalgam, protected by the above-mentioned electrolyte. Both the reference system and the protection layer must contain the ion which is to be determined. The reference systems may have several different cations incorporated at the same time. Further, it is mentioned that the tungsten bronze may contain other transition metals including vanadium. These electrode devices are sensitive to the oxygen pressure above the reference system. In the electrode device disclosed in GB 1 602 564, the reference system is constituted by two aluminium oxide phases covered with a further layer for fixing the oxygen potential, in order to reduce this oxygen sensitivity. Metal/metal oxide mixtures are suitable for this layer, e.g. of copper, chromium or nickel. Neither the operational stability nor the storage stability are particularly good for the sodium tungsten bronze.

In WO83/03304 (U.S. Pat. No. 4,632,732) a $H^{30}$-selective glass electrode device with a solid state, inner reference system is described preferably of biphased lithium vanadium bronze. It is mentioned that other lithium bronzes and sodium tungsten bronze may also be suitable. Such a lithium vanadium bronze as well as an electrode device including this must be prepared under anhydrous and oxygen-free conditions. Therefore, in practice, the electrode device will be complicated and expensive to prepare e.g. by thick film printing.

In U.S. Pat. No. 3,853,731 an ion selective glass electrode is described with a solid state reference system of a composite material of silver and silver halide. A paste of silver oxide and a silver salt of a halogen oxy acid fixed to the glass membrane is heated to obtain the composite material of silver and silver halide.

In U.S. Pat. No. 5,122,254 an $Na^+$-selective electrode device is described with a solid state electrolyte membrane containing sodium, zirconium, silicon etc. The solid state reference system consists of e.g. sodium tungsten bronzes, sodium molybdenum bronzes or sodium alloys. These must be biphased compounds. The electrode device can be prepared by thick film printing.

DE 41 12 301 describes a reference electrode comprising an alkali compound in a transition metal oxide, e.g. nickel oxide or cobalt oxide. This is very suitable for gas sensors. WO 95/22050 describes a reference electrode comprising an ion conductive solid state electrolyte, which is in contact with a glass phase.

DE 2 002 676 discloses an electrode device where the membrane consists of an ionic semiconductor, e.g. lanthanum fluoride, for measurement of fluoride. The reference system in such an electrode device may consist of e.g. lead or bismuth in epoxy polymer, which metals form an ionic semiconductor with fluoride.

Electrode devices for detection of gasses are also described. DE 43 24 922 and U.S. Pat. No. 5,112,456 disclose electrode devices for detection of oxygen which are based on various metal/metal oxide mixtures. U.S. Pat. No. 4,861,454 describes an electrode device for detection of oxygen which are based on a redox pair. Electrode devices for detection of $CO_2$ are described in U.S. Pat. No. 5,910, 239 and in U.S. Pat. No. 4,839,020. The first is based on stannate/titanate, and the other is of the Severinghaus-type, where the pH-electrode device is based on a reference system comprising a redox pair. In WO 96/12944 a thick film printed $CO_2$-sensor is described comprising copper oxide and titanium oxide.

Various bronzes with intercalated cations can also be used as selective materials in ion selective electrode devices. In such electrode devices, the bronze is both electron conductive and ion conductive, but the potential will also vary. Examples of this type of electrodes are disclosed in e.g. U.S. Pat. No. 3,825,482 and U.S. Pat. No. 3,856,634, wherein sodium tungsten bronze is used as selective electrode material.

Finally, in the report "Solid state sodium batteries" (Steen Skaarup and Keld West, *Energiministeriets Forskningsprogram: Energilagring*, Journ. No. 2263-407; 1443/85-2; 1443/86-3; 1443/87-4, April 1989), a research program is disclosed. The purpose of this was to characterise some potentially suitable sodium transition metal oxides for rechargeable batteries compared to for example lithium bronzes. Experiments have been carried out with, among others, sodium bronzes of molybdenum, chromium and vanadium with varying molar ratios between sodium, transition metal and oxygen. In the articles "Solid State Sodium Batteries" (S. .Skaarup et al., Proceedings of the *International Seminar on Solid State Ionic Devices*, edition B. V. R. Chowdari and S. Radhakrishna, Singapore, (1988) 75–86) and "Solid-State Sodium Cells—An Alternative To Lithium Cells?" (K. West et al.,*J. Power Sources* 26, 1989, pages 341–45) sodium vanadium bronzes are characterised for use in rechargeable batteries.

The previously proposed solid state, inner reference systems for replacement of the conventional inner reference systems containing a liquid still have certain disadvantages. Some systems impart to the electrode device an unsatisfactory stability, others are sensitive to redox active substances and $CO_2$. Some of the previously suggested reference systems impart acceptable properties, but requires expensive raw materials, are complicated to prepare or require preparation and use under controlled conditions. Thus there is still a need for electrode devices comprising a solid state, inner reference system with a stable potential and high sensitivity, where the reference system is further uncomplicated and economical to prepare and can be applied by methods which are suitable for miniaturisation such as thick film printing.

The object of the present invention is to provide an electrode device of the type mentioned in the introduction comprising a solid state, inner reference system which is economical and simple to prepare and at the same time imparts to the electrode device properties as regards for example sensitivity and stability, which are as good or better than the properties of known electrode devices. It is especially an object of the present invention to provide a planar, miniaturised electrode device with a solid state, inner reference system, which can be applied by thick film printing.

In accordance with this and according to the invention, an electrode device is obtained which comprises an ion selective material, a solid state, inner reference system of a bronze and a contact material. The reference system mediates the electrochemical correspondence between the ion selective material and the contact material. This electrode device is characterised in that the reference system comprises sodium vanadium bronze, where sodium is incorporated in the vanadium bronze at such a stoichiometric proportion that the insertion/liberation of sodium is reversible. An "ion selective material" is to be understood as a material which constitute a diffusion barrier against the surroundings, but which is sensitive to one or more ions of interest. The term "inner reference system" is to be understood as a system imparting to the electrode device a stable inner potential, as described above. Finally, the term "contact material" describes a material which is capable of mediating electrical contact between the inner reference system and usual measuring equipment, e.g. through an outer electric conductor. The "electrochemical correspondence" signifies the coupling between the ion transport and the electron transport The design of a preferred embodiment of the electrode device according to the invention is similar to the design of conventional ion selective electrode devices. It comprises an ion selective material aiming to segregate a particular sample from the inner part of the electrode device and at the same time allow the ion/ions in the sample, to which the material is sensitive, to affect the electrode device significantly. The ion selective material is also in contact with the solid state reference system so that an exchange current can be obtained between the ion selective material and the reference system. The solid state reference system is also in contact with the contact material so that it can mediate the electrochemical correspondence between the ion selective material and the contact material. When the electrode device according to the invention is used, the contact material is connected with usual measuring equipment, e.g. via an outer electric conductor. The content of the ion in the sample to be determined by the electrode device is read out on the measuring equipment.

Even though in the electrode device according to the invention the contact both between the ion selective material and the solid state reference system and between the solid state reference system and the contact material are presented as being direct, it must be understood that an electrode device comprising the solid state reference system in indirect contact with the Ion selective material and the contact material, respectively, also will be within the scope of the Invention, if only the solid state reference material is not thereby prevented from functioning as such.

The solid state, inner reference system in the electrode device according to the invention comprises vanadium bronze with sodium incorporated in the lattice of the bronze. The term "bronze" as used herein refers to ternary metal oxides with the formula $M_xT_yO_z$, which are electron conductive, and where T is a transition metal which is capable of being oxidised/reduced, and M is another or several other metals or hydrogen. x is an arbitrary value and represents the content of M per formula unit. y and z indicate the content of T and O respectively in the formula. In such bronzes the transition metal oxide is said to form the host structure and the other metal or hydrogen to be incorporated in this structure.

According to this, the sodium vanadium bronze in the electrode device according to the invention will have the formula $Na_xV_yO_z$, where the vanadium oxide forms the host structure and sodium is incorporated in this structure. At certain stoichiometric proportions between the three components, it is possible to obtain structures in which sodium can be reversibly inserted and liberated (further described in *Faststof-natriumbatterier*, Steen Skaarup and Keld West, *Energiministeriets Forskningsprogram: Energilagring*, Journ. No. 2263-407; 1443/85-2; 1443/86-3; 1443/87-4, April 1989). If this process is reversible, the sodium is said to be intercalated in the bronze, and the process is called an intercalation.

Surprisingly, it has been found that sodium vanadium bronzes with such stoichiometric proportions, that the incorporation of sodium is reversible, are very suitable for solid state, inner reference systems in electrode devices. Such reference system is capable of having electrons and sodium ions reversibly taken up and liberated across a phase boundary, and in this case the phase boundary between the reference system and the ion selective material. Thus the intercalation of sodium is connected with uptake and liberation of electrons. This property gives the bronze the ability to mediate the electrochemical correspondence.

The reference system of the electrode device according to the invention possesses thus surprisingly these potential stabilising properties in defiance of the fact that the sodium vanadium bronze is not biphased, which in the prior art is described to be preferred.

A solid state, inner reference system comprising sodium vanadium bronze has some further advantages. It is not sensitive to humidity, $CO_2$ or redox active substances such as oxygen. The bronze is then substantially insensitive to air humidity. Both the operational stability and the storage stability are excellent which is due to the fact that the system is neither sensitive to oxygen, $CO_2$, humidity nor evaporation of fluid. The use of sodium vanadium bronze as a solid state, inner reference system in the electrode device imparts that the preparation and the application of the reference system can take place under atmospheric air. This, combined with avoiding a liquid reservoir, makes it possible to use new, more simple and more efficient procedures of preparing the electrode devices according to the invention, e.g. thick film printing. The electrode devices according to the invention may be used at high temperatures as they do not comprise a liquid reservoir.

The lattice structure (and thus the unit cell) of sodium vanadium oxides may vary depending on the preparation conditions and the content of sodium. The sodium vanadium bronze for use in reference systems in electrode devices according to the invention are typically prepared by heating a mixture of $NaVO_3$ and $V_2O_5$ in a suitable molar ratio between 400 and 800° C. depending on the wanted structure. It is advantageous if the mixture of $NaVO_3$ and $V_2O_5$ is beforehand ground to a particle size smaller than 1 mm, and preferably smaller than 1 µm. By heating, a thermodynamically stable structure is obtained, which can be cooled to the ambient temperature. After cooling to 150° C. or below and under anhydrous and oxygen free conditions a further sodium Incorporation may result in a bronze which is no longer thermodynamically stable, but where the sodium incorporation is however reversible. When using the sodium vanadium bronze for reference systems in electrode devices according to the invention for potentiometric determination of an analyte it is however not particularly advantageous to make this subsequent intercalation.

According to a preferred embodiment of the invention, the reference system comprises thus sodium vanadium bronze of the formula $Na_xV_2O_5$, which is thermodynamically stable for $0.33<x<0.40$. After cooling to 150° C. or below and under anhydrous and oxygen free conditions, sodium may however by intercalation vary between x=0.01 and x=1.6 retaining approximately the same lattice structure and thus preserving the reversible conditions. This thermodynamically stable sodium vanadium bronze can be obtained by mixing $NaVO_3$ and $V_2O_5$ in a molar ratio of between 2:4 and 2:5 and heating to approximately 650° C. until equilibrium after which it can be cooled.

According to another preferred embodiment of the invention the reference system comprises sodium vanadium bronze of the formula (unit cell) $Na_{1+x}V_3O_8$. This structure can also be obtained by mixing $NaVO_3$ and $V_2O_5$ in a molar ratio of approximately 1:1 and heating to around 700° C. until equilibrium is reached. After cooling to 150° C. or below and under anhydrous and oxygen free conditions, sodium may however by intercalation vary between x=0 and x=2.2 retaining approximately the same lattice structure and thus preserving the reversible conditions.

Even though the above-mentioned structures are indicated with a formula representing an ideal stoichiometry between vanadium and oxygen, it must be understood that a bronze in which only the major part of the unit cells has this stated stoichiometry, also will fulfil the conditions of reversible incorporation of sodium and thus will also be within the scope of the invention. Accordingly, it is preferred that at least 90–95% of the bronze has a structure according to one of the formulas $Na_xV_2O_5$ or $Na_{1+x}V_3O_8$.

The above-mentioned limits for x are found under atmospheric air. However, it is likely that other limits for x can be found by modifying the preparation conditions and the conditions for use such as changing the oxygen partial pressure. Therefore these limits are just for stating preferred limits and not to limit the scope of the invention, since all sodium vanadium bronzes meeting the condition of reversible incorporation of sodium are suitable for reference systems in electrode devices according to the invention.

The bronze formed can be used as it is for a reference system in an electrode device, or it can be ground to a particle size with a diameter of from 0.001 µm to 100 µm, preferably from 0.1 µm to 10 µm, and particularly from 2 µm to 5 µm. This powder can then be pressed into a suitable shape, or it can be mixed with a suitable binder system to obtain a paste.

According to yet another preferred embodiment of the electrode device according to the invention, the bronze powder is mixed with a suitable binder system to obtain a paste which can be applied by methods suitable for miniaturisation. A suitable binder system is to be understood as a more or less viscous system binding the powder to a uniform mass. Such binder system typically comprises a suitable binder and various solvents and additives. One suitable binder system is the acrylate based S1112, which is accessible from ESL.

The purpose of the binder is to form a matrix for binding the bronze to obtain a reference system in solid form. For such binder systems, suitable binders which can be mentioned are polymers hardening by evaporation of solvent or by chemical reaction such as polyester, polymethacrylates, polyacrylates, butadiene acrylonitrile copolymer, polyvinyl chloride (PVC), polyurethane, polycarbonate, polyoxymethylene, polystyrene, polysiloxanes, epoxides, silicone, cellulose or cellulose derivatives, e.g. cellulose acetate, ethyl cellulose or propyl cellulose, or mixtures hereof.

Solvents and additives are added to give the paste the right application and hardening properties for the method chosen to prepare of the electrode device. They normally disappear or are consumed during hardening. Usable solvents are e.g. carbitol acetate or similar.

The properties of the above-mentioned paste comprising the bronze may be varied depending on the method of preparing the electrode device chosen. The viscosity of the paste before application is preferably from 0.2 Pa·s to 7,500 Pa·s, especially preferred from 2 Pa·s to 750 Pa·s, and for thick film printing advantageously from 100 Pa·s to 650 Pa·s. After hardening, the ratio between sodium vanadium bronze and binder system is preferably from 95:5 to 5:95 by weight, and especially preferred from 80:20 to 20:80 by weight.

The aforementioned reference system is suitable for electrode devices with sensitivity to various ions. The variety of ions which can be detected by the electrode device according to the invention are in principle only limited by which ions it is possible to prepare ion selective materials for.

Till now, it has been mentioned as an important condition for applicability of the electrode devices comprising known reference systems of the bronze type that the bronze should contain the ion to be detected (see e.g. GB 1 470 558; GB 1 521 964; GB 1 602 564 and U.S. Pat. No. 5,122,254). In accordance therewith, another surprising property of the reference system in the electrode device according to the invention is that the reference system is suitable for detecting a variety of ions and not only the ion contained in the reference system (here sodium).

The ion selective material can be any suitable Ion selective material, both of organic and inorganic nature. It should simply be capable of acting as a diffusion barrier towards the surroundings and at the same time be sensitive to one or more ions of interest.

The electrode device according to the invention can thus be used for detection of cations such as $H^+$, $Li^+$, $Na^+$, $K^+$, $Rb^+$, $Cs^+$, $NH_4^+$, $Mg^{2+}$, $Ca^{2+}$, $Sr^{2+}$, $Ba^{2+}$, $Ag^+$, $Pb^{2+}$, $Cd^{2+}$, $Ni^{2+}$ and $Co^{2+}$. It is also applicable for detection of other positively charged groups, such as the trimethylammonium ion, positively charged amino acids, positively charged nucleic acids or macromolecules comprising these, including pharmaceutical preparations.

According to yet another preferred embodiment of the invention, the electrode device comprises an ion selective material in the form of a membrane prepared from a polymeric material, where the membrane comprises an ionophore for one or more ions of interest and optionally a plasticizer. Among suitable ionophores, crown ethers can be mentioned, such as 18-crown-6 cryptands, for example 2,2,2-cryptand, calixarenes, for example 25,26,27,28-tetrakis(ethoxycarbonylmethoxy)-p-tert.butylcalix[4]arene, cyclic peptides, for example valinomycin and nonactin, noncylic multidentate amides, for example (−)-(R,R)-N,N'-(Bis(11-ethoxycarbonyl)undecyl)-N,N'-4,5-tetramethyl-3,6-dioxaoctanediamid (ETH 1001) and aliphatic amines, for example tridodecylamin. Suitable polymeric materials for the membrane are e.g. polyvinyl chloride, polymethacrylates, polyacrylates, silicones, polyesters or polyurethane or mixtures hereof. Among suitable plastlsizers can be mentioned di-octylsebacate and di-octylphthalate.

The contact material may comprise any suitable electron conductive material. Often it will comprise one or more precious metals, such as gold, palladium, platinum, rhodium or iridium and preferably gold or platinum, or mixtures hereof. Other suitable electron conductive materials are graphite or iron, nickel or stainless steel. The electron conductive material can be mixed with another component, such as a binder system having an advantageous effect on the properties of the contact material, both in connection with the preparation and the use of the electrode device.

The contact metal can be used as it is, e.g. as a metal wire, for contact material in an electrode device, or it can be ground to a particle size with diameter of from 0.001 $\mu$m to 100 $\mu$m, preferably of from 0.1 $\mu$m to 10 $\mu$m. This powder can then be pressed to a suitable form, or it can be mixed with a suitable binder system for obtaining a paste.

According to a preferred embodiment of the electrode device according to the invention, the contact metal in the form of powder is mixed with a suitable binder system to obtain a paste. Platinum paste is preferably used, such as P2607 (SIKEMA).

The electrode device according to the invention can be prepared as a conventional tubular electrode device or as a planar electrode device, which is provided on a support, the support being cut out in any shape desired. This electrode device is suitable for miniaturisation.

According to yet another preferred embodiment, the electrode device according to the invention is designed as a planar electrode device, which is provided on a support. The support can be made of any suitable material. However, it cannot be electron conductive and it must be able to resist the conditions under which the electrode device is hardened and used. The material usually comprises a ceramic or polymeric material.

Ceramic supports have the advantage that they are thermally, mechanically and chemically stable. If ceramic supports are used in combination with polymeric membranes, it may be necessary to use an adhesive material so that the membrane adheres to the adhesive material and the adhesive material adheres to the support. An example is disclosed in U.S. Pat. No. 5,844,200. Aluminum oxide and fosterite are ceramic materials which are suitable as supports.

Polymeric supports are more economic to use and may result in a better adhesion between polymeric membranes and support, than in the case of ceramic supports. Particularly good adhesion can be obtained if the membrane and the support are based on the same type of polymer. Polymeric supports also give less limitations on possible geometric designs than the ceramic support does. If polymeric supports are used, the hardening and use must often be carried out at lower temperatures. Among polymeric materials which may be suitable as supports can be mentioned polyvinyl chloride, polyester, polyimide(kapton), polymethylmethacrylate or polystyrene.

According to a preferred embodiment, the support can also constitute support for other electrode devices so that several electrode devices can be provided on one and the same support. For example an array of electrode devices sensitive to $Ca^{2+}$, $K^+$, $Na^+$ and $H^+$, respectively, can be provided. Such an array is suitable for simultaneous detection of all of said ions when present in the same sample, e.g. a blood sample.

The solid nature of the inner reference system opens up the possibility of preparing electrode devices according to the invention by new and more economic and efficient methods. Especially it is possible to prepare the electrode devices according to the invention by methods suitable for miniaturisation, such as by thick film printing, drop casting, spray coating or spincoating.

Thick film printing is particularly suitable for application of thin layers and in well-defined shapes, especially on plane surfaces. The thick film printing process resembles very much other printing processes such as screen printing. Briefly, a particular homogeneous paste is pressed through a screen with a suitable fineness and pattern on the surface which is to be covered. The desired pattern of the screen is generally obtained by first applying a photo sensitive emulsion to the screen which closes all the meshes. Then a negative illustrating the desired shape of the print is placed on top of the screen and this is developed resulting in the emulsion being dissolved in exposed areas. After rinsing the screen, it is ready for use. The fineness of the mesh and the thickness of the paste determines the thickness of the layer. The technique is further described in the book *Polymer Thick Film* (Ken, Gilleo. Edt. New York: Van Nostrand Reinhold, 1996) and in U.S. Pat. No. 5,844,200, in which the preparation of planar, miniaturised electrode devices prepared by thick film printing is disclosed. This technique is suitable for preparation of miniaturised, planar electrode devices and for mass production. Further, it is an advantage if the process can be carried out under atmospheric air.

A preferred embodiment of the electrode device according the invention is thus a planar, miniaturised electrode device prepared by thick film printing. Advantageous properties for such electrode devices are that they only require very small sample volumes, and that the method of preparation is suitable for mass production of electrode devices. If desired, only the contact material and the reference system are applied by thick film printing, after which the ion selective material is applied.

Another method suitable for preparing electrode devices according to the invention is spincoating. For instance a support similar to the above-mentioned can be spincoated with contact material of the type described above. Then a $V_2O_5$-xerogel prepared by ion exchange of $NaVO_3$ through a $H^+$-column can be spincoated on the contact material. After drying, the $V_2O_5$-xerogel can be impregnated by a NaCl-solution. $Na^+$ will spontaneously be absorbed until a composition corresponding to the unit formula $Na_{0.33}V_2O_5$ is obtained. A heat treatment at 650° C. stabilises the structure, Then a membrane can be dispensed above the bronze layer in the usual way.

A preferred embodiment of the electrode device according to the invention further comprises a reactive material, in which an ion product, to which the ion selective material is sensitive, can be formed from a particular analyte. By "reactive material" is meant a material which can be affected by a particular analyte resulting in a physical or chemical change. A particular analyte is any component which is present in a sample and for which it is desired to determine the content or presence. Among such electrode devices can be mentioned biosensors: and electrode devices of the Severinghaus-type.

In such a preferred embodiment of the electrode device according to the invention, the reactive material comprises a biological recognition component, where the recognition of a particular analyte occurs with formation of an ion product. The reactive material may be an integrated part of the membrane, or it may constitute a separate layer in the electrode device. The recognition component can e.g. be an enzyme, such as a hydrolase, drolase, an oxidase, or a reductase, or an antibody or a receptor, and the ion product to which the ion selective material is sensitive, can e.g. be $H^+$ or $NH_4^+$.

Another example of such a preferred electrode device according to the invention is an electrode device of the Severinghaus-type. The general design of electrode devices of the Severinghaus-type is described in the article "A Combined Transcutaneous $pO_2$ and $pCO_2$ Electrode With Electrochemical $HCO_3$ Stabilisation" by John W. Severinghaus, published in Journal of Applied Physiology, volume 51, No. 4, pages 1027–1032, March 1981, and in U.S. Pat. No. 4,836,907.

In electrode devices of this type, a gas which forms an acid or a base when contacted with water, diffuses into a reservoir with a more or less viscous aqueous electrolyte solution as reactive material. The pH-value in this fluid will then change relative to the partial pressure of the gas. If a pH-sensitive ($H^+$-selective) material is placed above the contact material and the reference system, this change can be detected, when at the same time the electrolyte solution is contact with a reference electrode, such as an Ag/AgCl-electrode.

The aqueous electrolyte solution preferably contains chloride ions and bicarbonate ions, for example in the form of KCl and $NaHCO_3$. The aqueous electrolyte may be based on aqueous glycol solutions, e.g. solutions of tetraethylene glycol, glycerol and ethylene glycol. Thickening agents can also be added, such as hydrocolloids, e.g. poly (vinylpyrrolidone), methylcellulose and ethyl cellulose, agar or similar.

Often, the reservoir will be segregated from the sample by a gas permeable diffusion barrier. This may e.g. be a membrane based on silicone, softened PVC or poly (tetrafluoroethylene). Among gasses which can be detected by this type of electrode device, $CO_2$ and $NH_3$ can be mentioned.

The electrode devices according to the invention disclosed above can also be prepared by methods which are suitable for miniaturisation as mentioned in connection with the ion selective electrode devices, and can therefore also be embodied as planar, miniaturised electrode devices.

Below, the invention will be illustrated further with reference to the drawing and the examples.

Figure 1:
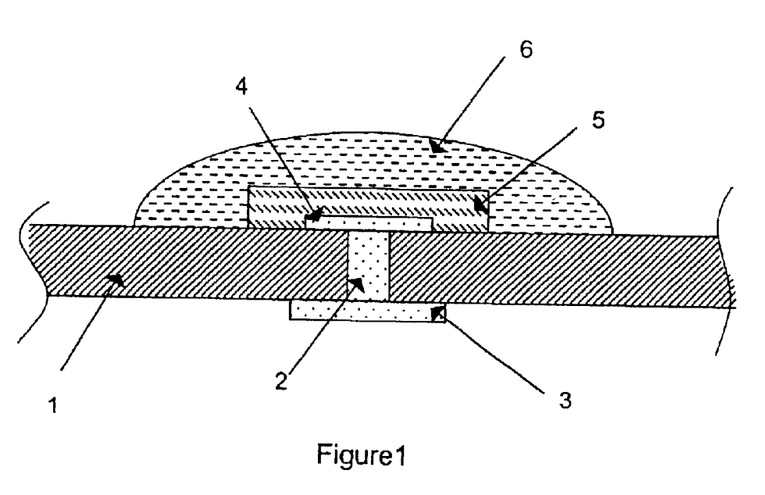
FIG. 1 illustrates a sectional view of a planar, miniaturised electrode device according to the invention of the ion selective type.

The ion selective electrode device according to the invention shown in FIG. 1 is of a type which can be characterised as a planar, miniaturised electrode device. The electrode device shown is provided on a polymeric support 1, of PVC. A hole with a diameter of 0.01 mm through the support is filled with platinum paste 2, as a contact material by thru-hole printing. This filling mediates electrical contact between a lower contact surface 3, of platinum paste on the one side of the support and an upper contact surface 4, of platinum paste on the other side of the support. The upper contact surface 4, of platinum paste is in contact with the reference system 5, of sodium vanadium bronze paste. The platinum paste is completely covered by the bronze paste. Above the reference system an ion selective PVC-membrane 6, is applied completely covering the reference system 5. The diameter of the electrode device is about 1.5 mm. During use of the electrode device, the lower contact surface 3, is connected with usual measuring equipment, e.g. via an outer electric conductor.

Figure 2:
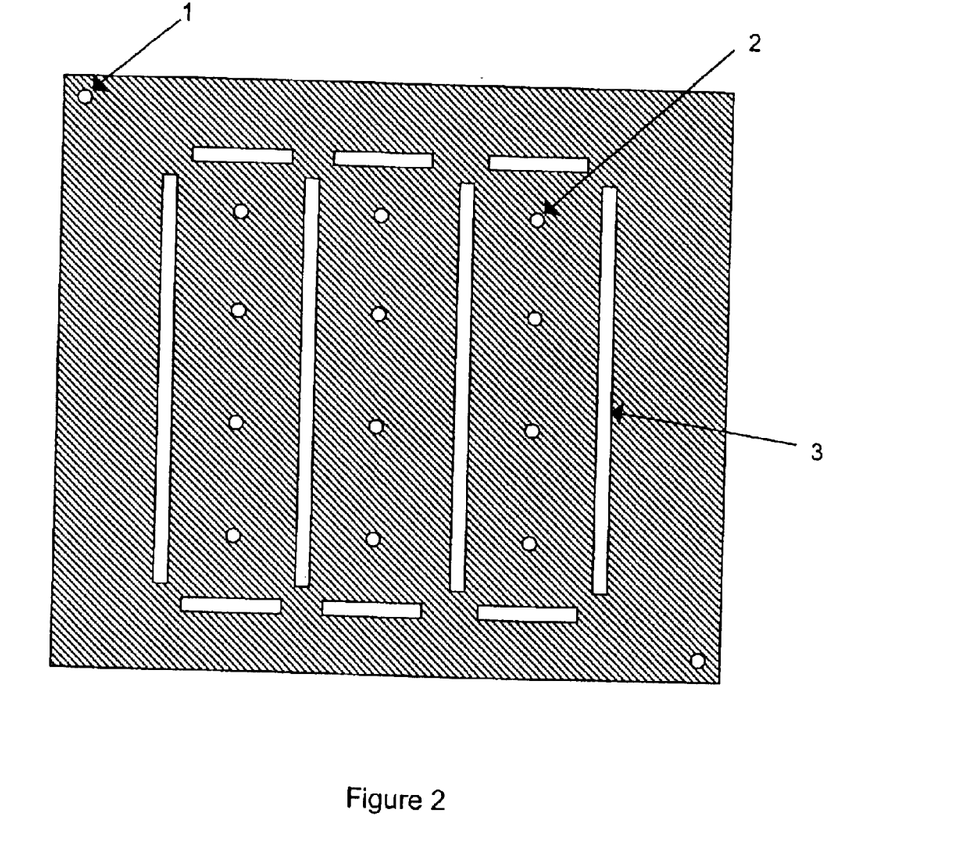
FIG. 2 illustrates the design of a support sheet suitable for thick film printing of a planar, miniaturised electrode device according to the invention.

FIG. 2 illustrates a support sheet suitable for thick film printing of planar, miniaturised electrode devices according to the invention. With the sheet, three arrays of four planar, miniaturised electrode devices according to the invention are obtained. The area of the plate is 2"×2", and it is approximately 0.9 mm thick. In two diagonal corners, positioning holes 1, are cut with laser as is known in the art for positioning the sheet in a thick film printing apparatus. Further, the white areas 3, and the 3×4 holes 2, with diameters of 0.01 mm and at intervals in the array of 1 cm are cut out with laser as is known in the art. If the sheet is cut out as indicated, each array constituting four electrode devices can easily be separated from the sheet after preparation of the electrode devices according to the invention. After careful cleaning, this sheet is ready for thick film printing of electrode devices of the type illustrated in FIG. 1.

Figure 3:
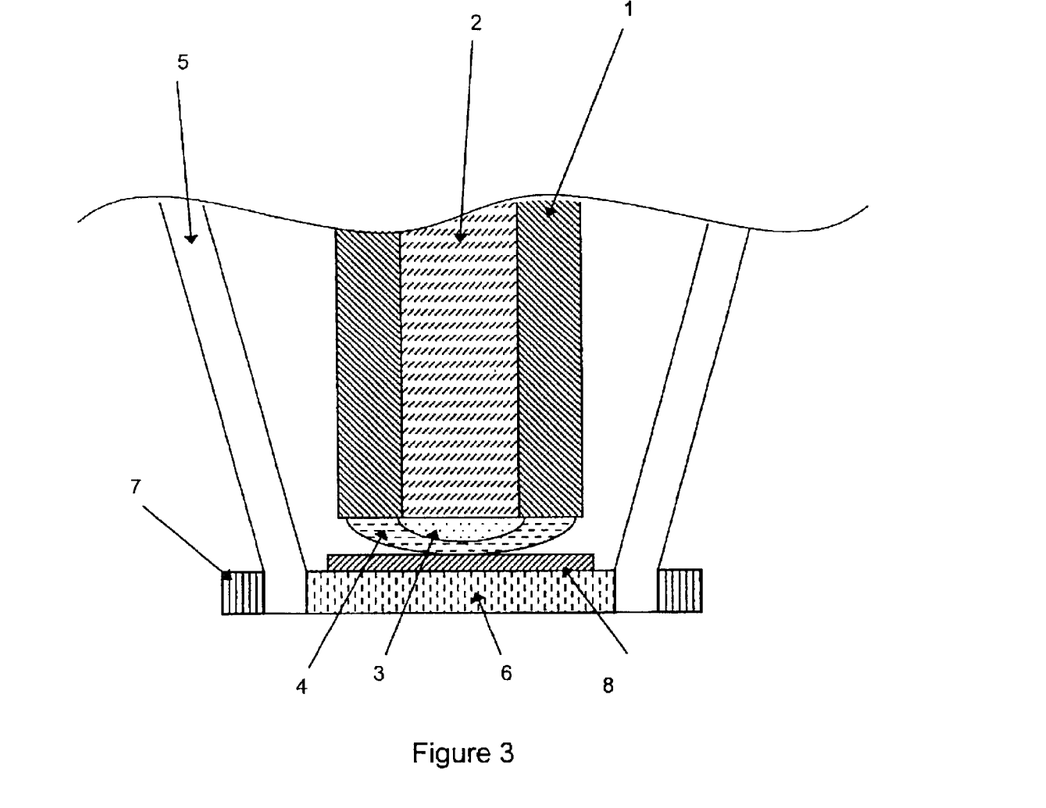
FIG. 3 illustrates a sectional view of a tubular electrode device according to the invention for detection of urea comprising an $NH_4^+$-selective part and a biologically active part.

The electrode device according to the invention illustrated in FIG. 3 for detection of urea can be characterised as a tubular electrode device. It includes an $NH_4^+$-selective part comprising an $NH_4^{30}$-selective material and a biologically active part comprising urease.

The $NH_4^+$-selective part of this electrode device is provided around a contact material 2, in the form of a brass pin plated with gold. The brass pin is surrounded by a tight-fitting insulating base 1, of PVC-tube. The brass pin is lowered 0.1 mm at one end, above which a reference system 3, of sodium vanadium bronze paste is applied, so that it covers the gold plated pin 2. Above the reference system 3, an $NH_4^+$-selective PVC membrane 4, is applied so that it covers the reference system 3.

The biologically active part comprising urease is provided around a conical jacket 5, of PVC. A polyester membrane 6, is glued to the jacket with a membrane ring 7, fixed around the end of the jacket. The membrane 6, is coated with a biologically active layer 8, comprising urease.

The $NH_4^+$-selective electrode device and the biologically active part is preferably assembled just before use. When assembled, the $NH_4^+$-selective part is pressed down in the biologically active part, whereby the $NH_4^+$-selective membrane is brought into contact with the urease layer and is fixed by means of a click-stop. During use, the other end of the brass pin is connected via a contact pin to an outer contact point, which again is connected with usual measuring equipment, e.g. via an outer electric conductor.

Figure 4A:
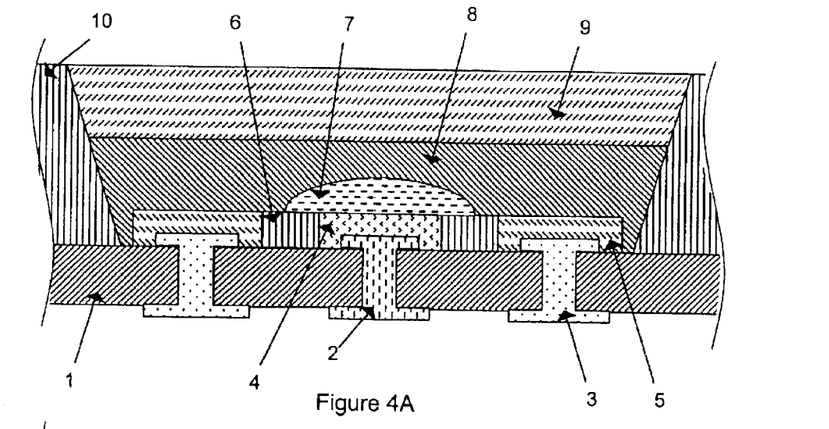
FIGS. 4A and B illustrate a sectional view of a planar, miniaturised electrode device of the Severinghaus-type according to the invention, and a top view of the same electrode device.
Figure 4B:
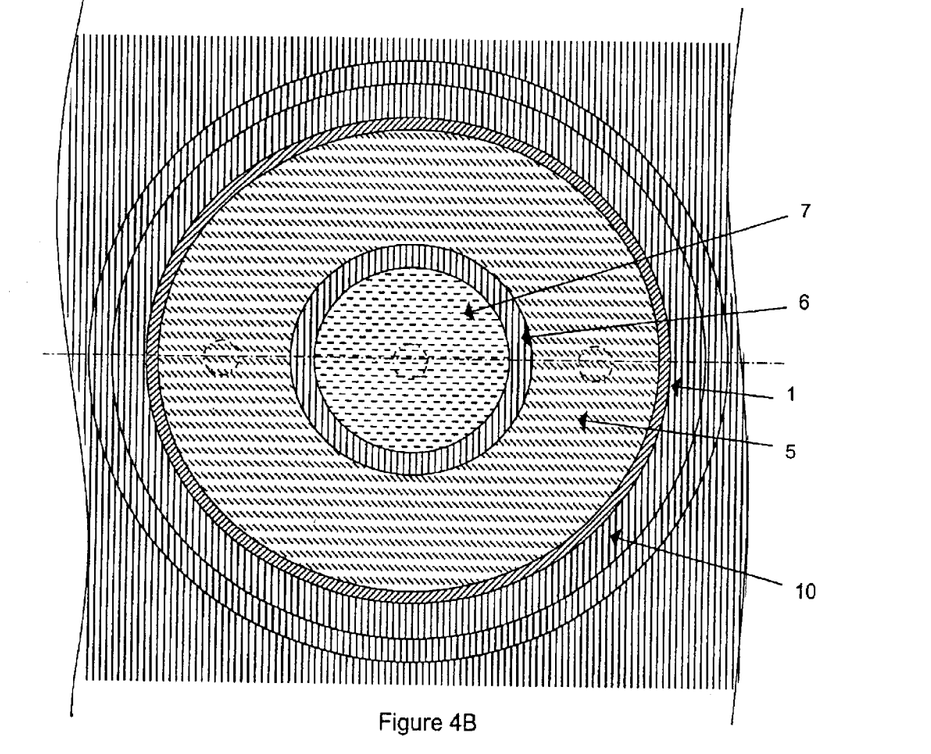

Finally, in FIGS. 4A and 4B is illustrated a planar, miniaturised electrode device of the Severinghaus-type for detection of $CO_2$. In FIG. 4A a sectional view of the electrode device is shown, and in FIG. 4B a top view is illustrated. The planar, miniaturised electrode device is provided on a ceramic support 1, which is prepared and processed as described in U.S. Pat. No. 5,844,200. Each individual electrode device is however provided around three holes positioned on a diagonal, as illustrated in FIG. 4B. The holes have diameters of 0.1 mm, and the two peripheral holes are placed in a distance of 0.9 mm from the central hole. Around the central hole, a $H^+$-selective electrode device is provided which is similar to the electrode device illustrated in FIG. 1. In a ring around the $H^+$-selective electrode device and separated from this with a dielectric material, a reference electrode is provided, which is based on the conventional Ag/AgCl reference system.

Around the central hole, the contact material 2, is thus constituted by a contact surface of platinum paste on each side of the support and a thru-hole filled with the same platinum paste for connecting the two contact surfaces with each other. The contact surface of platinum paste on the upper side of the support is covered with a layer of the reference system 4, of sodium vanadium bronze paste.

The layers of the contact material 2, and the reference system 4, are surrounded by a ring of a dielectric material 6, for isolation of these layers. Above the reference system 4, a $H^+$-selective PVC membrane 7, is applied completely covering the reference system 4, and reaching approximately half-way over the dielectric material 6. The dielectric material is constituted by a single layer of glass corresponding to layer 901 in U.S. Pat. No. 5,844,200 and of polymer layers corresponding to layers 1101 and 1103 in said patent.

The reference electrode is provided around the two peripheral holes. The contact material 3, of the reference electrode is thus constituted by a contact ring of silver paste around the dielectric material 6, and by two contact surfaces of silver paste on the lower side of the support around the peripheral holes and by a thru-hole filling of the holes with silver paste to connect the contact ring and contact surfaces with each other. The contact ring of silver paste is in contact with a ring of silver chloride paste 5. The contact ring of silver paste 3, is completely covered by the silver chloride paste 5.

The contact ring of silver paste 3, and the silver chloride paste 5, are again surrounded by a wall of a dielectric material 10. This outer wall of dielectric material 10 is supplied in such thick layer that it forms a high tapered wall; around the reference electrode. The dielectric material 10, is provided in the same way as the dielectric material 6.

The $H^+$-selective PVC membrane and the reference electrode are completely covered by a layer of aqueous electrolyte solution 8, containing chloride ions and bicarbonate ions. The electrolyte solution 8, is completely covered by a gas permeable silicone membrane 9. During use of the electrode device, the lower contact surface of platinum paste 2, and the lower contact surfaces of silver paste 3, are connected with usual measuring equipment, e.g. via outer electrical conductors.

Even though all these electrode devices are provided with a centrally placed contact material and reference system, this design should not be understood as a limitation of the scope of the invention.

Below an example is provided describing the preparation of sodium vanadium bronze for a reference system in electrode devices according to the invention. Furthermore, the use of this reference system is described for the preparation of various electrode devices according to the invention. Thus the preparation by thick film printing of planar, miniaturised electrode devices selective to $Ca^{2+}$, $K^+$, $Na^+$ and H+, respectively, is described, as well as the preparation of a tubular electrode device for detection of urea is described and finally the preparation by thick film printing of a planar, miniaturised electrode device of the Severinghaus-type for detection of $CO_2$ is described. These embodiments for electrode devices according to the invention are mere examples of preferred embodiments and should therefore not be understood as a limitation of the scope of the invention.

EXAMPLE 1

Bronze Paste for Solid State Reference System

First, the bronze is prepared, and then it is mixed with a suitable binder system:

Preparation of Sodium Vanadium Bronze of the Stoichiometry $Na_{0.33}V_2O_5$ 20.0 g $NaVO_3$ and 74.6 g $V_2O_5$ (molar ratio 2:5), both pro analysis, are carefully mixed in a mortar, and is quantitatively transferred to a nickel crucible. The crucible is put in an oven preheated to 400° C. Then the oven is heated to 650±10° C. with 100° C. per hour. When the 650° C. is reached, this temperature is maintained in another 5 hours. Then the oven is turned off, and the crucible with bronze is left in the oven overnight to cool down to the ambient temperature.

93.3 sodium vanadium bronze as a powder is obtained. The structure of the obtained product is analysed by X-ray powder diffraction, and the product is identified as $\beta$-$Na_{0.33}V_2O_5$ by comparison of the diffractogram with a standardised diffractogram of sodium vanadium bronze of the unit formula $\beta$-$Na_{0.33}V_2O_5$ (e.g. JCPDS-ICDD: Powder Diffraction, file #24-1155). The sodium content is further determined by flame photometry and the oxidation number of the vanadium (proportion between $V^{4+}$ and $V^{5+}$) is determined by titration with $KMnO_4$. The purity of the bronze is thus 98% $\beta$-$Na_{0.33}V_2O_5$.

When bronzes with other stoichiometric proportions are prepared, the proportion between the two starting materials is simply varied so that the desired Na/V-proportion is obtained. The appropriate quantity of oxygen will be emitted to the surroundings during heating, while the reaction mixture equilibrates at 650° C. for at least 5 hours.

Preparation of bronze paste for a solid state reference system

The sodium vanadium bronze prepared above is ground in a ball mill to a particle size of approximately 1 µm. This powder is then mixed in a ball mill with the binder system #1112S from ESL, which is a polymeric binder system based on acrylate in a ratio between bronze and binder system of 70:30 by weight. The paste is then ready for thick film printing.

EXAMPLE 2

Planar, Miniaturised Ion Selective Electrode Devices

First the preparation of membrane cocktails is disclosed to obtain a material being sensitive to $Ca^{2+}$, $K^+$, $H^+$ and $Na^+$, respectively. Then the design of the electrode device is disclosed.

Preparation of $Ca^{2+}$-Selective Membrane Cocktail

First a parent solution of polyvinyl chloride (PVC) is prepared. 2.0 g PVC (HMW PVC #81392, Fluka) is transferred to a 50 mL bluecap bottle. 4.0 g dioctylphthalate (DOP, #80030, Fluka) is transferred by a disposable pipette of plastic to the same bottle. 23.27 g distilled tetrahydrofuran (THF) and 7.76 g; cyclohexanone (CHX) is transferred to the bottle, which is a total of 4×the weight of the two first-mentioned ingredients. By this, a dry solids content of around 25 weight/weight % is obtained.

The bluecap bottle, which should be between half-full and full, is carefully closed with the cap. The bottle is placed in a beaker which is filled with water at ambient temperature until the water reaches a few mm above the mixture in the bottle. The mixture is stirred at 300 o/min., while within an hour it is heated to 60° C. The temperature is maintained at 60° C. for 20 minutes. It is important that the content of the bottle is not heated further, as the THF in the mixture is near the boiling point. The bottle is then left to cool down at ambient temperature.

This PVC parent solution has to be used the same day as it is heated.

50.0 mg of the ionophore ETH1001 (#21192, Fluka) is quantitatively transferred with a few drops of THF to a 50 mL bluecap bottle. Then 25.3 mg of the lipophilic salt potassium-tetra-p-chlorophenyl borate (K-tetrakis, #60591, Fluka) is weighed, corresponding to a molar ratio between lipophilic salt and ETH1001 of 0.7. This is quickly transferred into the bottle. 6.45 g PVC parent solution is weighed and is added to the mixture to obtain a concentration of ETH1001 of 3.1 weight/weight % of the dry solids content (ETH1001, DOP, PVC and lipophilic salt). This cocktail is stirred for two hours at ambient temperature and 300 o/min., after which it is ready for use. The cocktail must be stirred at ambient temperature until it is applied above the solid state reference system.

Preparation of $K^+$-Selective Membrane Cocktail 0.0589 g valinomycin, 2.53 dioctyl adipate (DOA, #2138, Fluka) and 0.96 g PVC ($M_w$=80,000 g/mol) are weighed and transferred to a bluecap bottle. After mixture of this with a magnetic stirrer, 9.18 g newly distilled, cooled THF and 3.05 CHX are added. Thereafter, a concentration of PVC is obtained of 7.1 weight/weight % and a total solids content (PVC+DOA) of around 26 weight/weight %. Subsequently, the solution is stirred at ambient temperature for at least 24 hours, after which it is ready for use. The cocktail must be stirred at ambient temperature until applied above the solid state reference system.

Preparation of $H^+$-Selective Membrane Cocktail 144 mg of the ionophore TDDA (#95292, Fluka) is weighed and transferred under Argon-atmosphere with a Hamilton syringe through the septum into a 50 mL bluecap bottle. 72 mg K-tetrakis, 1.6 g PVC ($M_w$80,000 g/mol) and 3.2 g DOP (#80030, Fluka) are weighed and transferred to the bottle. 16.40 g newly distilled, cooled THF and 5.47 CHX are weighed and transferred to the bottle, which in total corresponds to 4×the weight of the four first-mentioned ingredients. The bottle is carefully turned, so the fluid runs along the sides of the bottle, until all the components are mixed. The bottle must not be shaken or turned upside down.

A triangular magnetic stirrer is put in the bottle, and the cocktail is stirred at high speed and ambient temperature for 18 hours. The cocktail must be stirred at ambient temperature until applied above the solid state reference system.

Preparation of $Na^+$-Selective Membrane Cocktail 60 mg of the ionophore calixarene (#71747, Fluka), 0.5 g PVC ($M_w$=80,000 g/mol) and 1.0 g DOP (#80030, Fluka)

are weighed and transferred to a 50 mL bluecap bottle. 4.69 newly distilled, cooled THF and 1.56 CHX are weighed and transferred to the bottle, which in total corresponds to 4×the weight of the three first-mentioned ingredients. The bottle is carefully turned, so the fluid runs along the sides of the bottle, until all the components are mixed. The bottle must not be shaken are turned upside down.

A triangular magnetic stirrer is put in the bottle, and the cocktail is stirred at high speed and ambient temperature for 24 hours. The cocktail must be stirred at ambient temperature until applied above the solid state reference system.

Preparation of Polymeric Support for Thick Film Printing of Planar, Miniaturised Ion Selective Electrode Devices A sheet of support of 2"×2"is cut out of a 0.9 mm thick PVC-sheet, which is extruded from granulate of the type Norvinyl 224 (Norsk Hydro). For the preparation of arrays of planar, miniaturised electrode devices, the support is cut as illustrated in FIG. 2. In two diagonal corners, positioning holes for positioning of the sheet in a thick film printing apparatus is cut with laser as is known in the art The hatched sections and the 3×4 holes in arrays with diameter 0.01 mm and at intervals of 1 cm are also cut out.

The support is then cleaned by ultrasonic treatment for five minutes in Deconex (Borer Chemie AG)/deionised water, volume ratio, 1:10, and then for 2×5 minutes in deionised water. Then it is left at ambient temperature for drying overnight. The surfaces of the support must not be touched or polluted in other ways.

Application of Contact Material and Solid State Reference System by Thick Film Printing For thick film printing of the reference electrode according to the invention, a thick film printing apparatus (TF-100, MPM Corp.) is used. A squegee with a hardness of 70 Shore is used. Further, screens prepared by ScreenTech are used with a fineness of 200 mesh. The screens are custom designed, with a pattern which is adapted to the cutting of the support and the shapes of the paste material required for each electrode device. As fine meshes are used, it is important that the printing process is performed in surroundings with a limited amount of particles in the air.

For the preparation of planar, miniaturised electrode devices according to the invention and illustrated in FIG. 1, a PVC-sheet is used as support as described above and illustrated in FIG. 2. At first the contact material of platinum paste is applied (P2607, SIKEMA). This is done three times. At first, on the upper side of the support, a contact surface is printed having a diameter of 0.03 mm (decided by the pattern of the screen) over each hole through the support. Vacuum is applied behind the hole for 10 seconds to establish the thru-hole. This print is left to level for 10–15 minutes. Then it is hardened in an oven at 50° C. for 90±10 minutes. On the lower side of the support, a contact surface of platinum paste with a diameter of 0.04 mm is then printed above each hole. Then vacuum is again applied behind the hole for 10 seconds to establish the thru-hole. This layer is leveled and hardened by same process as before. A layer thickness of 25 $\mu$m is obtained. On the upper side of the support above the previous print another layer of platinum paste is printed using the same mesh as for the first print. This time without applying vacuum behind the hole. Once more the same leveling and hardening process is used. A total layer thickness of the upper contact surface of platinum paste of 75 $\mu$m is obtained.

On the upper side of the support the above prepared bronze paste is then printed on top of the platinum paste so that the contact surface is completely covered by the bronze paste to obtain a diameter of approximately 0.07 mm. Also this print is left to level for 10-1 minutes, after which it is dried in an oven at 50° C. for 90±10 minutes. Subsequently, another layer is printed using the same mesh and the same levelling and hardening process to obtain a layer thickness of 75 $\mu$m. The printing of the bronze paste is carried out without applying vacuum behind the hole.

Then the membrane cocktails are applied as described below.

Application of Membrane Cocktails

The procedure for application of membrane cocktail is the same no matter which of the prepared cocktails are to be applied.

Under microscope a circle of approximately 2.5 mm diameter is stamped in the support around the thick film printed solid state reference system to limit the flow of the membrane cocktail.

The membrane cocktail is taken from the stirrer and vented under vacuum until no more air is liberated from the cocktail. The bottle is left with the cap on for approximately 15 minutes until ambient temperature has been reached.

Approximately 1.5 $\mu$L of the membrane cocktail is applied by a suitable dispensing method (e.g. with a rotary dispenser, such as Digispense 2000, IVEK). After drying in an oven at 40° C. for at least 15 minutes, another approximately 1.5 $\mu$L membrane cocktail is applied. After standing for approximately ½ minute, the electrode device is dried again in an oven at 40° C. for 24±1 hour.

Preparation of an Array of Electrode Devices

On the support described above an array of electrode devices is constituted by 4 holes on a row (see FIG. 2), which have been thick film printed with contact material and solid state reference system around these holes as described above. Over each of the four respective reference systems either a $K^+$-, $Na^+$-, $Ca^{2+}$- or $H^+$-selective membrane cocktail is applied, as described above.

Mounting of Measuring Chamber

After at least 24 hours of hardening of the membrane at ambient temperature, each array is cut free from the support with a scalpel. Under a microscope an array is glued into a measuring chamber as described in U.S. Pat. No. 5,844,200 so that the array constitutes one wall of the measuring chamber. The membranes should not be in direct physical contact with the other walls of the chamber.

EXAMPLE 3

Electrode Device for Detection of Urea

This electrode device is designed as a tube-shaped $NH_4^+$-selective electrode device combined with a biologically active part as illustrated in FIG. 3. At first, the preparation of the $NH_4^+$-selective material is disdosed and then the design of the actual electrode device.

Preparation of $NH_4^+$-Selective Membrane Cocktail 4.30 g distilled DOA (#2138, Fluka), 1.64 g PVC ($M_w$= 80.000 g/mol) and 9.85 g THF are transferred to a 50 mL bluecap bottle. The mixture is stirred for 24–30 hours. Then it is heated while stirred on a water bath to 60° C. for 30 minutes. During constant stirring and after cooling to ambient temperature, 0.100 g Nonactin (Fluka) is added. This mixture is stirred for minimum 24 hours and until applied above the solid state reference system.

Preparation of Tubular $NH_4^+$-Selective Electrode Device

A brass pin which is nickel-plated and then drum gilt at Chembo Overfladeteknik and has a diameter of 2 mm and a length of 1 cm is inserted into an injection-moulded tube of hard PVC with an internal diameter of 2 mm, an outer diameter of 6 mm and a length of 1.5 cm so that the tip of the brass pin is lowered 0.1 mm compared to the end surface of the PCV-tube. Above the gold-plated tip of the brass pin, a layer of the above-disclosed sodium vanadium bronze paste is applied using thick film technique, so that the gold-plated tip is completely covered. The paste layer must be approximately 50–100 $\mu$m thick. The paste is then hardened in an oven at 60° C. for 90 minutes. This causes the vanadium bronze layer to shrink to a thickness of 40–80 $\mu$m. The $NH_4^+$-selective membrane cocktail is applied after venting as described above.

Preparation of Biologically Active Part

In the biologically active part, the biologically active component is the enzyme urease. The urease is applied as a solution. It is prepared as follows:

A parent solution with 30 weight % sucrose is prepared by dissolving 6.43 g sucrose (#9378, Sigma, 342.3 g/mol) In 15.0 mL deionised water. 1.34 mL of this parent solution is mixed with 0.66 mL deionised water and 219 mg solid urease preparation (#232-656-0, URE3, Biozyme, 4.57×10$^5$ units/g). Thus 2 mL of a solution with 50 kU/mL urease in 20 weight % sucrose is obtained.

This solution is applied dropwise so that 9 drops of 30 nL is apportioned with an interval of 1.1 mm over a square area on a membrane. A polyethylene glocol(PEG)-coated polyethylene terephthalate (PETP)-membrane (Mylar Grade A, Whatman) with a thickness of 12 $\mu$m is used as membrane. It has a pore density of 1×10$^7$ pores/cm$^2$ and a pore diameter of approximately 0.1 $\mu$m.

After application of the enzyme solution, the membrane is glued with cyanoacrylate above the lower part of a conical jacket having an upper diameter of 11 mm and a lower diameter of 9 mm. The membrane is then fixed with a membrane ring of nylon (Nylon 6, DSM). The jacket is moulded in PVC (Arnite D 02-300, DSM) and is equipped with means which can be part of a click-stop.

Preparation of Electrode Device for Detection of Urea

The $NH_4^+$-selective electrode device and the biologically active part are assembled preferably just before use. At the assembling the other end of the brass pin is connected via a flexible contact spear (#SPGR-2-B-4-G S/C, IDI) to an outer contact point, which is incorporated in a base equipped with means to be part of a click-stop. The $NH_4^+$-selective electrode device is pressed down into the biologically active part almost like a piston, until a locking means in the form of a click-stop is activated. This makes sure that the $NH_4^+$-selective membrane is kept pressed down against the urease layer, so the transfer rate of the $NH_4^+$ from the enzyme layer to the $NH_4^+$-selective membrane is satisfactory.

EXAMPLE 4

Planar, Miniaturised Electrode Devices of the Severinghaus-Type for Detection of $CO_2$ A ceramic support is prepared and processed as described In U.S. Pat. No. 5,844,200. It thus consists of 96% aluminium oxide. Each individual electrode device is however provided around three holes situated on a diagonal, as illustrated in FIG. 4B. The holes have diameters of 0.1 mm, and the two peripheral holes are placed at a distance of 0.9 mm from the central hole. The design of the electrode device is described below.

Design of the Electrode Device

The planar, miniaturised electrode devices according to the invention of the Severinghaus-type for detection of $CO_2$ is provided on the above-mentioned ceramic material. For the thick film printing the same apparatus as before is used. At first the dielectric material is thick film printed as disclosed in U.S. Pat. No. 5,844,200. The cone-shaped outer sidewall is designed as described and with a small diameter of 2.5 mm and a large diameter of .2.7 m. A ring of the dielectric material is also printed with an Internal diameter of 0.5 mm and an outer diameter of 1.3 mm for separation of the pH-electrode and the reference electrode. The first layer is a thin glass layer (ESL 4904, ESL), which in the US-patent has the reference no. 901.

Above the glass layer, a polymer layer with the reference no. 1101 is printed three times to obtain a layer thickness of 0.05 mm. The polymeric paste for thick film printing is composed of 28.1% of a low molecular weight polymethylmethacrylate (#2041, Dupont), 36.4% carbitol acetate, 34.3% silanised kaolin (HF900, Engelhard), 0.2% pyrogenic silica and 1% trimethoxysilane, all by weight. The same paste is used to make 10 prints making up another polymer layer with the reference no. 1103 in U.S. Pat. No. 5,844,200. However, this layer is not printed on the ring for separation of the pH-electrode and the reference electrode. A total layer thickness of around 0.15 mm is obtained.

The platinum paste and the bronze paste are applied over the central hole as described in example 2. The silver paste is applied above the two peripheral holes corre sponding to the procedure described for the platinum paste. However, the upper contact surface is applied in a circle around the platinum paste with an inner diameter of 1.3 mm and an outer diameter of 1.9 mm. In the same way, a double layer of silver chloride paste (#C2DR50, MCA Services) is printed above this ring.

The cone-shaped groove is then filled with an aqueous electrolyte solution for obtaining a layer thickness of 0.05 mm. The electrolyte solution is constituted by an aqueous 50 weight/weight % glycol solution with a concentration of KCl of 20 mM and of $NaHCO_3$ of 10 mM, to which the thickener poly(vinylpyrrolidon) is added to obtain a viscosity of around 2000 Pa·s.

The electrolyte solution is covered by a 0.05 mm thick silicone membrane (TSE GE 399C, General Electrics, diluted with n-hexane), which is added by dispensing.

EXAMPLE 5

Results

The electrode devices according to the invention are tested as regards sensitivity and stability on calibration fluids containing both $H^+$, $Na^+$, $K^+$ and $Ca^{2+}$ in clinically relevant concentrations. They are also tested on blood samples as regards precision and repeatability.

The electrode devices are tested in the commercially available blood gas analysis instruments ABL500 and ABL700 (RADIOMETER MEDICAL A/S) equipped with the electrode devices according to the invention instead of the commercially available ones. All measurements are made at 37° C.

For the ion selective electrode devices according to example 2, sensitivities of 93-98% of the value obtained by the Nernst-equation are obtained. This corresponds to the sensitivities of the conventional electrode devices containing a liquid.

The operational stability of the electrode devices according to example 2 are determined over a period of 75 days by continuous injection of a calibration fluid ($[Na^+]$=50 mM, $[Ca^{2+}]$=5 mM, $[K^+]$=10 mM, pH=6.8). During the first 2–5 days a conditioning of the electrode devices takes place, which means that their electrode potentials in this period drop by 20–50 mV. Afterwards, the electrode potentials increase approximately linearly by 0.2–2.4 mV/day, which corresponds to the stability of the conventional electrode devices containing a liquid.

After storage of the ion selective electrode devices according to example 2 for 6 months, no reduction of the sensitivity or operational stability were found when testing the electrode devices.

When measuring blood samples of unknown composition and comparing with results obtained with commercially available electrode devices, the electrode devices according to example 2 have proven to be as good as the similar commercially available electrode devices as regards precision and repeatability and better with regard to storage stability.

In interference tests, the solid state, inner reference system has proven to be insensitive to variations in the partial pressures of $CO_2$ and $CO_2$.

With the urea sensor according to example 3, an electrode device is obtained which can be used in the physiologically relevant measuring range 1–50 mM. The operational stability is determined over a period of 1 month. The electrode potential drops by about 100 mV over the first 3 weeks and then stays constant, whereas the Nemst sensitivity is constant at about 97% over a month. The urea sensitivity drops evenly by about 35% over 1 month.

The storage stability of the $NH_4^+$-selective part of the urea sensor is as described for the other ion selective electrode devices. Interference from $Na^+$ and especially $K^+$ has been observed.

| List of Suppliers | |
|---|---|
| Biozyme Laboratories | USA, California, San Diego, CA 92131-1029, 9939 Hibert Street, Suite 101 |
| DSM | The Netherlands, 6130 AA Sittard, Poststraat 1, P.O Box 43 |
| Engelhard Corporation | USA, New Jersey, Iselin, NJ 08830, 101 Wood Avenue |
| ESL (Electroscience Laboratories) | USA, California, Ventura CA 93003, 6085 Sikorsky St. |
| Fluka (Sigma-Aldrich) | USA, Milwaukee, WI 53201, Mail: P.O. Box 2060, Milwaukee, WI 53233, 1001 West St. Paul Avenue |
| IDI (Interconnect Devices, Inc.) | USA, Kansas 66106, Kansas City, 5105 Richland Avenue |
| MCA Services | Great Britain, SG8 6EJ, South Cambridgeshire, Melbourn, Moat Lane, Melbourn Science Park, Units 1A & 1B |
| MPM Corp. (Speedline Technologies, Inc.) | USA, Maine, Franklin, MA 02038, 16 Forge Park |
| RADIOMETER MEDICAL A/S | Denmark, DK-2700 Brønshøj, Åkandevej 21 |
| SIKEMA/ABLESTICK | Sweden, Box 32001, 12611 Stockholm |

-continued

| List of Suppliers | |
|---|---|
| Screen Tech. A/S | Denmark, 3450 Allerød, Sneppevang 3 |
| Norsk Hydro | Norway, Norsk Hydro ASA N-0240 Oslo, Bygdøy Allé 2 |

What is claimed is:

1. An electrode device comprising an ion selective material, a solid state, inner reference system of a bronze and a contact material, where the reference system mediates the electrochemical correspondence between the ion selective material and the contact material, characterized in that the reference system comprises sodium vanadium bronze, where the sodium is incorporated in the vanadium bronze at such a stoichiometric proportion that the insertion/liberation of sodium is reversible.

2. The electrode device according to claim 1, characterized in that the reference system comprises sodium vanadium bronze of the formula $Na_xV_2O_5$, where $0.01<x<1.6$.

3. The electrode device according to claim 1, characterized in that the reference system comprises sodium vanadium bronze of the formula $Na_xV_2O_5$, where $0.3<x<0.4$.

4. The electrode device according to claim 1 characterized in that the reference system comprises sodium vanadium bronze of the formula $Na_{1+x}V_3O_8$, where $0.01<x<2.2$.

5. The electrode device according to claim 1, characterized in that the reference system comprises the sodium vanadium bronze of a particle size with a diameter of from 0.01 μm to 100 μm, and preferably from 0.1 μm to 10 μm.

6. The electrode device according to claim 1, characterized in that the reference system is prepared from a paste comprising the sodium vanadium bronze mixed with an appropriate binder system.

7. The electrode device according to claim 6, characterized in that the binder system comprises a polymeric binder hardening by evaporation of solvent or by chemical reaction, such as polyester, polymethacrylates, polyacrylates, butadiene acrylonitrile copolymer, polyvinyl chloride, polyurethane, polycarbonate, polyoxymethylene, polystyrene, polysiloxanes, epoxides, cellulose or cellulose derivatives, e.g. cellulose acetate, ethyl cellulose or propyl cellulose, or mixtures hereof.

8. The electrode device according to claim 6, characterized in that the reference system comprises the sodium vanadium bronze and the binder at a weight ratio of between 80:20 and 20:80.

9. The electrode device according to claim 1, characterized in that the ion selective material is sensitive to an ion chosen among $H^+$, $Li^+$, $Na^+$, $K^+$, $Rb^+$, $Cs^+$, $NH_4^+$, $Mg^{2+}$, $Ca^{2+}$, $Sr^{2+}$, $Ba^{2+}$, $Ag^+$, $Pb^{2+}$, $Cd^{2+}$, $Ni^{2+}$ and $Co^{2+}$.

10. The electrode device according to claim 1, characterized in that the ion selective material is sensitive to an ion chosen among $H^+$, $Li^+$, $K^+$, $Rb^+$, $Cs^+$, $NH_4^+$, $Mg^{2+}$, $Ca^{2+}$, $Sr^{2+}$, $Ba^{2+}$, $Ag^+$, $Pb^{2+}$, $Cd^{2+}$, $Ni^{2+}$ and $Co^{2+}$.

11. The electrode device according to claim 1, characterized in that the ion selective material is a polymer membrane comprising an ionophore for one or more ions.

12. The electrode device according to claim 11, characterized in that the polymer membrane comprises polyvinyl chloride, polymethacrylates, polyacrylates, silicones, polyester or polyurethane or mixtures hereof.

13. The electrode device according to claim 1, characterized in that the contact material comprises a contact metal of a noble metal, such as gold, palladium, platinum, rhodium or iridium or mixtures thereof.

14. The electrode device according to claim 13, characterized in that the contact material is prepared from a paste comprising the contact metal mixed with an appropriate binder system.

15. The electrode device according to claim 1, characterized in that it is designed as a planar electrode device provided on a support.

16. The electrode device according to claim 15, characterized in that the support comprises ceramic or polymer materials.

17. The electrode device according to claim 15, characterized in that the support also constitutes support for other electrode devices.

18. The electrode device according to claim 17, characterized in that the electrode device and the other electrode devices each are sensitive to different ions chosen from the group of $Ca^{2+}$, $K^+$, $Na^+$, amd $H^+$ and that the electrode devices are prepared on a common support in an array.

19. The electrode device according to claim 1, characterized in that it further comprises a reactive material, in which a particular analyte is reacted under formation of an ion product, to which the ion selective material is sensitive.

20. The electrode device according to claim 19, characterized in that the reactive material comprises a biological recognition component.

21. The electrode device according to claim 20, characterized in that the biological recognition component is an enzyme.

22. The electrode device according to claim 21 characterized in that the enzyme is urease and the ion selective material is sensitive to $NH_4^+$.

23. The electrode device according to claim 19, characterized in that the reactive material is an aqueous electrolyte solution the pH of which changes relative to the partial pressure of a specified gas, e.g. $CO_2$ or $NH_3$, and that the ion selective material is a pH-sensitive material, and that the aqueous electrolyte solution mediates the contact between the pH-sensitive material and a reference electrode.

24. The electrode device according to claim 22, characterized in that it comprises a gas permeable barrier facing the surroundings.

25. The electrode device according to claim 1, characterized in that the contact material and the reference system are applied by a thick film printing.

26. A method of preparing an electrode device comprising an ion selective material, a solid state, inner reference system of a bronze and a contact material, where the reference system mediates the electrochemical correspondence between the ion selective material and the contact material, comprising using a sodium vanadium bronze for the reference system in which the sodium is incorporated in the vanadium bronze at such a stoichiometric proportion that the insertion/liberation of sodium is reversible.

* * * * *